United States Patent
Pfeiffer et al.

(10) Patent No.: US 7,821,637 B1
(45) Date of Patent: Oct. 26, 2010

(54) SYSTEM FOR CONTROLLING INTENSITY OF A BEAM OF ELECTROMAGNETIC RADIATION AND METHOD FOR INVESTIGATING MATERIALS WITH LOW SPECULAR REFLECTANCE AND/OR ARE DEPOLARIZING

(75) Inventors: Galen L. Pfeiffer, Lincoln, NE (US); Martin M. Liphardt, Lincoln, NE (US); James N. Hilfiker, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 470 days.

(21) Appl. No.: 12/070,824

(22) Filed: Feb. 21, 2008

Related U.S. Application Data

(60) Provisional application No. 60/902,942, filed on Feb. 22, 2007, provisional application No. 60/918,633, filed on Mar. 19, 2007.

(51) Int. Cl.
*G01J 4/00* (2006.01)

(52) U.S. Cl. .............. 356/367; 356/364; 356/369; 356/370

(58) Field of Classification Search ......... 356/364–370, 356/239.8, 369, 491, 213; 257/21, 432
See application file for complete search history.

(56) References Cited

U.S. PATENT DOCUMENTS

| | | | |
|---|---|---|---|
| 4,097,110 A | 6/1978 | Carey ................ 350/149 |
| 4,203,670 A * | 5/1980 | Bromberg ............ 356/367 |
| 4,434,025 A | 2/1984 | Robillard ............ 156/601 |
| 4,563,367 A | 1/1986 | Sherman ............. 427/39 |
| 5,011,706 A | 4/1991 | Tarhay et al. ......... 427/39 |
| 5,131,752 A | 7/1992 | Yu et al. ............ 356/369 |
| 5,221,364 A | 6/1993 | Hotaling ............. 136/249 |
| 5,246,782 A | 9/1993 | Kennedy et al. ....... 428/421 |
| 5,303,709 A | 4/1994 | Dreher .............. 128/665 |
| 5,418,019 A | 5/1995 | Chen et al. .......... 427/579 |
| 5,787,890 A | 8/1998 | Reiter et al. ........ 128/665 |
| 5,821,171 A | 10/1998 | Hong et al. .......... 438/767 |
| 5,903,047 A | 5/1999 | Liao et al. .......... 257/632 |
| 5,936,734 A * | 8/1999 | Johs et al. .......... 356/364 |
| 6,049,220 A | 4/2000 | Borden et al. ........ 324/765 |
| 6,080,683 A | 6/2000 | Faur et al. .......... 438/770 |
| 6,112,114 A | 8/2000 | Dreher .............. 600/476 |
| 6,124,545 A | 9/2000 | Bauer et al. ......... 136/255 |
| 6,156,967 A | 12/2000 | Ralph et al. ......... 136/244 |
| 6,165,875 A | 12/2000 | Fonash et al. ........ 438/486 |
| 6,200,825 B1 | 3/2001 | Yoshimi et al. ....... 438/24 |
| 6,297,134 B1 | 10/2001 | Ui et al. ............ 438/563 |
| 6,300,141 B1 | 10/2001 | Segal et al. ......... 436/518 |
| 6,362,414 B1 | 3/2002 | Fujisawa et al. ...... 136/256 |
| 6,395,973 B2 | 5/2002 | Fujisawa et al. ...... 136/256 |
| 6,407,327 B1 | 6/2002 | Ralph et al. ......... 136/244 |
| 6,444,898 B1 | 9/2002 | Fujisawa et al. ...... 136/256 |
| 6,498,380 B1 | 12/2002 | Otani et al. ......... 257/432 |
| 6,521,826 B2 | 2/2003 | Wada ................ 136/255 |
| 6,593,077 B2 | 7/2003 | Faur et al. .......... 430/770 |
| 6,613,697 B1 | 9/2003 | Faur et al. .......... 438/770 |
| 6,620,631 B1 | 9/2003 | Tao et al. ........... 438/9 |
| 6,662,570 B2 | 12/2003 | Venkatasubramanian ... 62/3.2 |

(Continued)

*Primary Examiner*—Tarifur Chowdhury
*Assistant Examiner*—Michael LaPage
(74) *Attorney, Agent, or Firm*—James D. Welch

(57) ABSTRACT

Disclosed is a system for controlling focus, angle of incidence and intensity of an electromagnetic beam over a spectrum of wavelengths, and methodology for optimizing investigation of samples which demonstrate low specular reflectance and/or are depolarizing of a polarized beam of electromagnetic radiation, such as solar cells.

3 Claims, 3 Drawing Sheets

U.S. PATENT DOCUMENTS

| | | |
|---|---|---|
| 6,693,711 B1 | 2/2004 | Leger et al. ............... 356/369 |
| 6,710,366 B1 | 3/2004 | Lee et al. ................... 257/14 |
| 6,716,656 B2 | 4/2004 | Shtein et al. ............... 438/24 |
| 6,722,140 B2 | 4/2004 | Venkatasubramanian ...... 62/3.2 |
| 6,738,139 B1 | 5/2004 | Synowicki et al. .......... 356/369 |
| 6,777,706 B1 | 8/2004 | Tessler et al. ............... 257/17 |
| 6,798,511 B1 | 9/2004 | Zhan et al. ................. 356/369 |
| 6,812,047 B1 | 11/2004 | Borden et al. ............... 438/16 |
| 6,819,845 B2 | 11/2004 | Lee et al. ................... 385/122 |
| 6,855,369 B2 | 2/2005 | Nakamura et al. .......... 427/164 |
| 6,885,444 B2 | 4/2005 | Borden et al. ............ 356/239.8 |
| 6,885,458 B2 | 4/2005 | Borden et al. ............... 356/502 |
| 6,911,349 B2 | 6/2005 | Li et al. ..................... 438/16 |
| 6,934,024 B2 | 8/2005 | Zhan et al. ................. 356/369 |
| 6,946,161 B2 | 9/2005 | Yamada et al. ............. 427/226 |
| 6,961,499 B2 | 11/2005 | Lee et al. ................... 385/122 |
| 7,005,669 B1 | 2/2006 | Lee ............................ 257/21 |
| 7,011,871 B2 | 3/2006 | Herron et al. ............... 428/1.4 |
| 7,020,372 B2 | 3/2006 | Lee et al. ................... 385/129 |
| 7,039,556 B2 | 5/2006 | Whitefield et al. .......... 702/183 |
| 7,049,004 B2 | 5/2006 | Domash et al. ............. 428/446 |
| 7,061,561 B2 | 6/2006 | Silverstein et al. .......... 349/117 |
| 7,083,835 B2 | 8/2006 | Elman et al. ................ 428/1.3 |
| 7,125,926 B2 | 10/2006 | Satoh et al. ................. 524/502 |
| 7,130,055 B2 | 10/2006 | Borden et al. ............... 356/491 |
| 7,141,489 B2 | 11/2006 | Burgener, II et al. ........ 438/478 |
| 7,144,803 B2 | 12/2006 | Engbrecht et al. ........... 438/622 |
| 7,160,809 B2 | 1/2007 | Hamers et al. .............. 438/695 |
| 7,161,173 B2 | 1/2007 | Burgener, II et al. .......... 257/43 |
| 7,163,724 B2 | 1/2007 | Elman et al. ................ 428/1.3 |
| 7,164,077 B2 | 1/2007 | Venkatasubramanian .... 136/203 |
| 7,170,574 B2 | 1/2007 | Tan et al. .................... 349/117 |
| 7,187,443 B1 | 3/2007 | Synowicki et al. .......... 356/369 |
| 7,202,143 B1 | 4/2007 | Naseem et al. .............. 438/486 |
| 7,211,304 B2 | 5/2007 | Elman et al. ................ 428/1.3 |
| 7,221,420 B2 | 5/2007 | Silverstein et al. .......... 349/117 |
| 7,224,527 B2 | 5/2007 | Koike et al. ................. 359/584 |
| 7,226,966 B2 | 6/2007 | Kambe et al. ............... 524/432 |
| 7,227,196 B2 | 6/2007 | Burgener, II et al. ........ 257/103 |
| 7,235,154 B2 | 6/2007 | Dalrymple et al. ..... 156/345.13 |
| 7,235,735 B2 | 6/2007 | Venkatasubraman-ian et al. ..................... 136/203 |
| 7,236,221 B2 | 6/2007 | Ishikawa et al. ............ 349/119 |
| 7,238,596 B2 | 7/2007 | Kouvetakis et al. ......... 438/507 |
| 7,282,798 B2 | 10/2007 | Venkatasubramanian .... 257/713 |
| 7,288,296 B2 | 10/2007 | Elman et al. ................ 428/1.3 |
| 7,289,211 B1 * | 10/2007 | Walsh et al. ................ 356/369 |
| 7,489,400 B1 * | 2/2009 | He et al. ..................... 356/369 |
| 2001/0005554 A1 | 6/2001 | Nakamura et al. |
| 2001/0025649 A1 | 10/2001 | Wada |
| 2002/0053395 A1 | 5/2002 | Ui et al. |
| 2002/0091323 A1 | 7/2002 | Dreher |
| 2003/0020912 A1 * | 1/2003 | Norton et al. ............... 356/369 |
| 2003/0027433 A1 | 2/2003 | Faur et al. |
| 2003/0031438 A1 | 2/2003 | Kambe et al. |
| 2003/0087121 A1 | 5/2003 | Domash et al. |
| 2003/0087471 A1 | 5/2003 | Shtein et al. |
| 2003/0178057 A1 | 9/2003 | Fujii et al. |
| 2003/0227623 A1 | 12/2003 | Zhan et al. |
| 2004/0058079 A1 | 3/2004 | Yamada et al. |
| 2004/0058468 A1 | 3/2004 | Takahashi et al. |
| 2004/0062945 A1 | 4/2004 | Domash et al. |
| 2004/0103937 A1 | 6/2004 | Bilyalov et al. |
| 2004/0179158 A1 | 9/2004 | Silverstein et al. |
| 2004/0186216 A1 | 9/2004 | Satoh et al. |
| 2004/0189992 A9 | 9/2004 | Zhan et al. |
| 2004/0208350 A1 | 10/2004 | Rea et al. |
| 2004/0259353 A1 | 12/2004 | Engbrecht et al. |
| 2005/0012095 A1 | 1/2005 | Niira et al. |
| 2005/0022863 A1 | 2/2005 | Agostinelli et al. |
| 2005/0024561 A1 | 2/2005 | Elman et al. |
| 2005/0052119 A1 | 3/2005 | Yu et al. |
| 2005/0106713 A1 | 5/2005 | Phan et al. |
| 2005/0109238 A1 | 5/2005 | Yamaki et al. |
| 2005/0128391 A1 | 6/2005 | Tan et al. |
| 2005/0150599 A1 | 7/2005 | Dalrymple et al. |
| 2005/0184287 A1 | 8/2005 | Herron et al. |
| 2005/0186495 A1 | 8/2005 | Herron et al. |
| 2005/0187411 A1 | 8/2005 | Herron et al. |
| 2005/0189015 A1 | 9/2005 | Rohatgi et al. |
| 2005/0195486 A1 | 9/2005 | Sasaki et al. |
| 2005/0227465 A1 | 10/2005 | Smith et al. |
| 2005/0270458 A1 | 12/2005 | Ishikawa et al. |
| 2005/0270459 A1 | 12/2005 | Elman et al. |
| 2005/0286001 A1 | 12/2005 | Elman et al. |
| 2005/0288896 A1 | 12/2005 | Whitefield |
| 2006/0099135 A1 | 5/2006 | Yodh et al. |
| 2006/0108688 A1 | 5/2006 | Richardson et al. |
| 2006/0115640 A1 | 6/2006 | Yodh et al. |
| 2006/0141466 A1 | 6/2006 | Pinet et al. |
| 2006/0174935 A1 | 8/2006 | Sawada et al. |
| 2006/0193975 A1 | 8/2006 | Elman et al. |
| 2006/0203164 A1 | 9/2006 | Silverstein et al. |
| 2006/0209566 A1 | 9/2006 | Koike et al. |
| 2006/0215158 A1 | 9/2006 | Saitoh |
| 2006/0231827 A1 | 10/2006 | Hanato et al. |
| 2006/0276047 A1 | 12/2006 | Ouyang et al. |
| 2007/0001151 A1 | 1/2007 | Sapochak et al. |
| 2007/0004220 A1 | 1/2007 | Tran Quoc et al. |
| 2007/0006915 A1 | 1/2007 | Nakajima et al. |
| 2007/0128370 A1 | 6/2007 | Takada et al. |
| 2007/0157966 A1 | 7/2007 | Meguro et al. |
| 2007/0172978 A1 | 7/2007 | Chua et al. |
| 2007/0190305 A1 | 8/2007 | Yamaki et al. |
| 2007/0208123 A1 | 9/2007 | Kambe et al. |
| 2007/0221914 A1 | 9/2007 | Becker et al. |
| 2007/0227586 A1 | 10/2007 | Zapalac, Jr. |
| 2007/0228364 A1 | 10/2007 | Radu et al. |
| 2007/0232065 A1 | 10/2007 | Basol |
| 2007/0232782 A1 | 10/2007 | Radu et al. |
| 2007/0235133 A1 | 10/2007 | Benassi |
| 2007/0241670 A1 | 10/2007 | Sapochak et al. |
| 2007/0258147 A1 | 11/2007 | Van Der Boom et al. |
| 2008/0015269 A1 | 1/2008 | Bazan et al. |
| 2008/0022896 A1 | 1/2008 | Karkkainen |
| 2008/0032602 A1 | 2/2008 | Dalrymple et al. |

* cited by examiner

SYSTEM FOR CONTROLLING INTENSITY OF A BEAM OF ELECTROMAGNETIC RADIATION AND METHOD FOR INVESTIGATING MATERIALS WITH LOW SPECULAR REFLECTANCE AND/OR ARE DEPOLARIZING

CROSS-REFERENCE TO RELATED APPLICATIONS

This Application Claims Benefit of Provisional Application Ser. Nos. 60/902,942 Filed Feb. 22, 2007 and 60/918,633 filed Mar. 19, 2007.

BACKGROUND

It is known that sources of electromagnetic radiation vary as regards output intensity vs. wavelength. Further, it is known that detectors of electromagnetic radiation become saturated when too high an intensity is input thereto. Where the intensity of one or more a wavelengths in a spectrum of wavelengths is high enough to saturate a detector, one approach is to attenuate the intensity of all wavelengths. This can be accomplished by a Neutral density filter, but neutral density filters do not pass UV wavelengths. Problems develop using this approach in that reducing the intensity of the highest intensity wavelengths can cause reduction of the intensity of other wavelengths below that which a detector can detect. Another approach to reducing intensity is to pass a beam of electromagnetic radiation through an iris which can be reduced in opening size, however, non-uniformity in the beam can lead to non-uniform results.

It is also disclosed that ellipsometers and polarimeters and the like typically comprise a source of a beam of electromagnetic radiation, a beam polarizer, an analyzer and a detector arranged so that a beam provided by the source passes through the polarizer, impinges on a sample and the passes through he analyzer and into the detector. The beam polarizer sets a polarization state in said beam which is changed by interaction with a sample, and the analyzer selects polarization states which are passed to the detector.

Conventional practice of ellipsometry involves directing a polarized beam of electromagnetic radiation, which can be focused or not, at a sample surface at a set angle of incidence, and detecting the resulting electromagnetic radiation after its interaction with the sample with a detector. Change in polarization state of the beam provides insight into the sample composition. Typically there is no need to consider that the beam leaving a sample might not be sufficiently intense for a detector to detect, or that it might be so intense, at least at one or more wavelengths in a spectroscopic range of wavelengths, that the detector becomes saturated. However, when applying ellipsometry to samples which do not uniformly reflect specularly, such as new generation solar cells, these concerns become very important. The present invention focuses on adjusting ellipsometer systems to "optimize" signal detection when "difficult" samples are investigated, rather than on setting parameters, such as angle of incidence and beam focusing based on some other criteria.

Patents identified which include the terms "solar cell" and "ellipsometry" or "ellipsometer" were identified and are:

U.S. Pat. Nos. 7,282,798; 7,238,596; 7,235,735; 7,235,154; 7,227,196; 7,224,527; 7,202,143; 7,187,443; 7,164,077; 7,161,173; 7,160,809; 7,144,303; 7,141,489; 7,130,055; 7,125,926; 7,049,004; 7,020,372; 7,005,669; 6,961,499; 6,946,161; 6,911,349; 6,885,458; 6,885,444; 6,819,845; 6,812,047; 6,777,706; 6,738,139; 6,722,140; 6,716,656; 6,710,366; 6,662,570; 6,620,631; 6,613,697; 6,593,077; 6,521,826; 6,498,380; 6,444,8.98; 6,359,973; 6,362,414; 6,300,141; 6,200,825; 6,165,875; 6,124,545; 6,080,683; 6,049,220; 5,821,171; 5,418,019; 5,221,364; 5,131,752; 5,011,706;

U.S. Pat. No. 7,226,966; 7,039,556; 7,011,871; 6,855,369; 6,407,327; 6,297,134; 6,156,967; 5,903,047; 5,246,782, 4,563,367; 4,434,025;

Published Patent Applications identified which include the terms "solar cell" and "ellipsometry" or "ellipsometer" were identified and are:

20080022896; 20070232782; 20070228364; 20070202123; 20070190305; 20070157966; 20070128370; 20050288896; 20050227465; 20050195486; 20050189015; 20050187411; 20050186495; 20050184287; 20050199238; 20050052119; 20050022863; 20040186216; 20030178057; 20030031438; 20020053395; 20010005554;

20080032602; 20080015269; 20070258147; 20070241670; 20070235133; 20070232065; 20070227586; 20070221914; 20070172978; 20070006915; 20070004220; 20070001151; 20060276047; 20060231827; 20060209566; 20060174935; 20060108688; 20050150599; 20050106713; 20050022863; 20050012095; 20040259353; 20040186216; 20040103937; 20040062945; 20040058468; 20040058079; 20030087471; 20030087121; 20030027433; 20010025649; 20010013361.

As the system of the present invention includes crossed-polarizers, patents identified which include the terms "crossed-polarizer" and "ellipsometry" or "ellipsometer" were identified and are:

U.S. Pat. Nos. 7,236,221; 7,221,420; 7,211,304; 7,163,724; 7,083,835; 7,061,561; 6,934,024; 6,798,511; 6,693,711; 6,112,114; 5,787,890; 5,303,709; 4,097,110; 7,170,574;

2006/0215158; 2006/0203164; 2006/0193975; 2005/0286001; 2005/0270459; 2005/0270458; 2005/0024561; 2004/0189992; 2004/0179158; 2003/0227623; 2003/0227623; 2002/0091323; 2006/0141466; 2006/0115640; 2006/0099135; 2005/0270458; 2005/0128391; 2004/0208350; 2004/0189992; 2003/0227623; 2002/0091323.

It is believed that the foregoing identified prior art is the most relevant to be found and has as its major thrust the application of conventional ellipsometry to the measurement of various parameters such as common to solar cells. Even in view of the prior art, however, need remains for improved systems and improved methodology which better enable application of ellipsometry to the investigation of sample characterizing parameters of samples which demonstrate low specular reflectance and/or which are depolarizing, via, on a case by case basis, controlling selection(s) from the group of: intensity, focus, and angle of incidence of a beam of spectroscopic electromagnetic radiation used to investigate said materials.

DISCLOSURE OF THE INVENTION

The present invention is best disclosed in the context of spectroscopic ellipsometers or polarimeters or the like. With that in mind it is noted that conventional practice of ellipsometry comprises directing a beam of electromagnetic radiation in a known polarization state onto a sample surface along at least one known angle of incidence, then detecting reflected or transmitted electromagnetic radiation which is in an altered state of polarization as a result of interaction with said sample. The beam can also be subjected to focusing onto the sample. It is important to understand that typical reasons for setting an angle of incidence are based on a criteria of optimizing contrast between how a sample affects orthogonal, (ie. "P" and "S" components which are referenced to the plane of the sample surface), of the polarized beam so that the magnitude of their ratio is optimized. Focusing is typically applied to allow investigating specific locations on a sample. It is also known to control of the intensity of a beam of electromagnetic radiation, including emphasizing the intensity of some wavelengths over others, which interacts with a sample to optimize detection by a detector. This is typically done by increasing the source intensity where an increase is in intensity is required, or by insertion of attenuating filters where beam intensity must be decreased. It is also known to cause a beam to reflect off, for instance, a. silicon substrate with an oxide on its surface to provide emphasized IR and UV intensities with respect to Visible.

The present invention also controls parameters such as angle of incidence, focusing and beam intensity, but for reasons different than those disclosed above. The present invention is concerned with using ellipsometry to investigate samples which are difficult to investigate as, for instance, they reflect non-specularly and/or are depolarizing. When difficult samples are investigated it can occur that intensity of a beam entering a detector after interaction with a sample does not have sufficient intensity, or has too high an intensity to be well detected. The present invention teaches that beam intensity at a detector can be "optimized" by adjusting the angle of incidence or focusing/defocusing of the beam incident on the sample. In addition, the present invention teaches a new, effectively "crossed polarizer" approach in ellipsometry, to attenuating beam intensity at a location near the source of the beam. Said new approach can further involve application of a compensator between the crossed polarizers to modify intensity vs. wavelength characteristics.

In view of the above, it is disclosed that the present invention system adds a novel "control polarizer", and preferably a sequentially located "control compensator" adjacent to a Source of a beam of electromagnetic radiation to a typical ellipsometer or polarimeter system which comprises a source of a beam of electromagnetic radiation, a beam polarizer, an analyzer and a detector which are arranged so that a beam provided by the source passes through the beam polarizer, impinges on a sample and the passes through the analyzer and into the detector. The novel control polarizer is positioned before the beam polarizer and in use is rotated with respect to the beam polarizer to substantially uniformly attenuate the intensity of all wavelengths which pass through said beam polarizer. When present a control compensator between the control and beam polarizers can beneficially be applied to cause selective attenuation of some wavelengths in the spectrum more than others. This can provide utility where less attenuated wavelengths are best to probe sample characteristics.

The present invention system then comprises a system for controlling the intensity of a beam of electromagnetic radiation as a function of wavelength, comprising a source of a polychromatic beam of electromagnetic radiation and a sequence of control and beam polarizers, said control and beam polarizers being rotatable with respect to one another. In use the beam polarizer is caused to set a polarization state in a beam exiting therefrom, and the control polarizer is rotated with respect to said beam polarizer to substantially uniformly control the intensity of the beam exiting the beam polarizer over a spectrum of wavelengths. The system can further comprise a control compensator between said control and beam polarizers which serves to cause selective attenuation of some wavelengths more than others in said spectrum of wavelengths. Said system further comprises an analyzer and a detector such that in use the polarized beam exiting said beam polarizer interacts with a sample and then passes through said analyzer and into said detector, and said system is an ellipsometer or polarimeter.

Said system can further comprise at least one system compensator between said beam polarizer and said analyzer.

A method of controlling the intensity of a beam of electromagnetism over a spectral range, comprising the steps of:

a) providing a system for controlling the intensity of a beam of electromagnetic radiation as described above;

b) setting a beam polarization state with the beam polarizer and rotating the control polarizer with respect thereto to control the intensity.

Said method can further comprise:

c) providing said control compensator between said control and beam polarizers and adjusting its orientation so that attenuation of the intensity of some wavelengths in said spectrum is greater than is that of others.

The present invention is also directed toward facilitating investigation of materials which demonstrate low specular reflectance and/or are depolarizing of a polarized beam of electromagnetic radiation, such as solar cells. As opposed to a need to attenuate beam intensity, it can also be difficult to provide a beam of sufficient intensity to such materials so that a beam reflecting therefrom can be efficiently detected. Approaches to optimizing detector input can include varying the angle of incidence of a beam to a sample surface, as well as controlling the amount of focus provided to a beam by a focusing element. Said approaches are often applied to investigation of samples for the purposes other than optimizing detector input, but it is believed that the present invention usage is new, novel and non-obvious. For instance, conventional uses of focusing are to simply investigate a smaller region on a sample. The present invention, however, utilizes varying focus to increase intensity of a reflected beam which is incident upon the sample.

Continuing, a method of investigating materials demonstrating low specular reflectance using electromagnetic beams, comprising a procedure which comprises steps a, b and c, said steps a, b and c being:

a) providing a system comprising:

a source of electromagnetic radiation;

a variable focusing means;

a low specular reflectance material sample;

a detector of electromagnetic radiation;

arranged such that said source of electromagnetic radiation provides a beam of electromagnetic radiation which is directed to pass through said variable focusing means and impinge on said low specular reflectance sample at an angle of incidence thereto, partially reflect from said low specular reflectance material sample and enter said detector of electromagnetic radiation such that said detector develops an output signal;

b) while monitoring said output signal from said detector, varying the angle of incidence and degree of focusing provided by said variable focusing means, to determine a combination thereof which substantially optimizes said output signal;

c) with the system configured as determined in steps a and b, obtaining data from the detector.

Said method further comprising steps d and e, said steps d and e being:

d) practicing steps a and b to the end that the detector signal output is substantially optimized, and e) obtaining data from said detector by practice of step c.

Said method can further comprise providing at lest one selection from the group:

a variable filter between said source of electromagnetic radiation and said detector, and a system comprising a control polarizer and a beam polarizer between said source and said sample;

a system comprising a control polarizer, a control compensator and a beam polarizer between said source and said sample;

which can be applied to control the intensity of the electromagnetic radiation entering said detector;

and in which said method further includes the step of:

adjusting the selection to place the intensity of said electromagnetic radiation entering said detector into a range which does not saturate it.

It is noted that when a control polarizer, a control compensator and a beam polarizer are present between said source and said sample, typically an analyzer will be present between the sample and detector and the system will be an ellipsometer or polarimeter.

Said method can be characterized by at least one selection from the group consisting of:

at least some obtained data is stored in machine readable media;

at least some obtained data is displayed electronically or by non-electronic means;

at least some obtained data is caused to be represented by a signal which is applied to provide a concrete and tangible result.

It is noted that while data from the detector will typically be obtained over many wavelengths and many angles of incidence, the present invention method, as recited above, preferably fixes the angle of incidence based on optimizing the electromagnetic radiation intensity which enters the detector. It has been preliminary determined that a relatively large angle of incidence, (e.g. greater than about 75 degrees), typically leads to increased intensity in electromagnetic radiation reflecting from low reflectivity materials.

In general, it is to be understood that typical parameters which are determined by such a described procedure are ellipsometric PSI and ellipsometric DELTA which are defined by:

$$\frac{r_p}{r_s} = \rho = \tan\Psi \cdot \exp(i \cdot \Delta)$$

Continuing, said parameters can be applied in, for instance, well known regression procedures to determine values of such as refractive index (n), extinction coefficient (k) and thickness of one or more thin film layers on a substrate. When investigating a non-depolarizing sample the value for PSI and DELTA are sufficient to allow its characterization. However, where a depolarizing sample is investigated an additional parameter is also typically calculated as 1.0 minus the square root of the sum of the squares of:

$$\% DEP = 1 - \sqrt{N^2 + C^2 + S^2}$$

where:

$N = \cos(2\psi)$;

$C = \sin(2\psi) \cos(\Delta)$; and $S = \sin(2\psi) \sin(\Delta)$.

It has been found that a depolarization of about 35% can be tolerated but that extremely high values thereof are not desirable. A method of investigating materials which cause depolarization of electromagnetic beams comprising a procedure which comprises steps a, b and c, said steps a, b and c being:

a) providing a system comprising:

a source of electromagnetic radiation;

a variable focusing means;

a depolarizing material sample;

a detector of electromagnetic radiation;

arranged such that said source of electromagnetic radiation provides a beam of electromagnetic radiation which is directed to pass through said variable focusing means and impinge on said depolarizing sample at an angle of incidence thereto, partially reflect from said depolarizing material sample and enter said detector of electromagnetic radiation such that said detector develops an output signal;

b) while monitoring said output signal from said detector and determining depolarization of the beam entering thereinto, varying the angle of incidence and degree of focusing provided by said variable focusing means, to determine a combination thereof which substantially minimizes depolarization associated with an output signal;

c) with the system configured as determined in steps a and b, obtaining data from the detector;

said method further comprising steps d and e, said steps d and e being:

d) practicing steps a and b to the end that the detector signal output represents an acceptable amount of beam depolarization, and e) obtaining data from said detector by practice of step c.

Said method can further comprise providing at least one selection from the group:

a variable filter between said source of electromagnetic radiation and said detector, and a system comprising a control polarizer and a beam polarizer between said source and said sample;

a system comprising a control polarizer, a control compensator and a beam polarizer between said source and said sample;

which can be applied to control the intensity of the electromagnetic radiation entering said detector.

This is because in the rare cases, where a source of electromagnetic radiation provides beam of sufficient intensity to cause the electromagnetic radiation reflected from low reflectivity material being investigated, or in the case where depolarizing material is being investigated, it can be necessary that the procedure further comprise applying a means for attenuating beam intensity, (ie. a variable filter or the control polarizer and control compensator), between said source of electromagnetic radiation and said detector, which is applied to control the intensity of the electromagnetic radiation entering said detector. The method then further includes adjusting the variable filter or the control polarizer and control compensator to place the intensity of said electromagnetic radiation entering said detector into a range which does not saturate it.

It is again noted that when a control polarizer, a control compensator and a beam polarizer are present between said source and said sample, typically an analyzer will be present between the sample and detector and the system will be an ellipsometer or polarimeter.

Said method can be characterized by at least one selection from the group consisting of:
- at least some obtained data is stored in machine readable media;
- at least some obtained data is displayed electronically or by non-electronic means;
- at least some obtained data is caused to be represented by a signal which is applied to provide a concrete and tangible result.

For general insight it is noted the combination of the control and beam polarizer operates like two pieces of polarized material which allow essentially all electromagnetic radiation directed theretoward to pass through when they are aligned, but block more and more of said electromagnetic radiation as said two pieces of polarized material are rotated with respect to one another to place them so that their directions of polarization are directed orthogonally.

Finally, where an ellipsometer system comprises the control polarizer, a control compensator and a beam polarizer present between said source and said sample in an ellipsometer or polarimeter system, a beneficial approach to application is to cause a beam of electromagnetic radiation to pass through said components and reflect from a specularly reflecting sample, and adjust the control polarizer and control compensator to reduce the intensity exiting the beam polarizer so that a detector, which receives the electromagentic radiation reflecting from said sample, is not saturated. The precedure can then involve replacing the sample with a non-specular sample and if necessary rotating the control polarizer to increase the intensity arriving at the sample. This allows the intensity to be increased when necessary by backing off the effect of the control polarizer and control compensator.

The present invention will be better understood by reference to the Detailed Description Section of this Specification, in conjunction with the Drawings.

DETAILED DESCRIPTION

Figure 1:
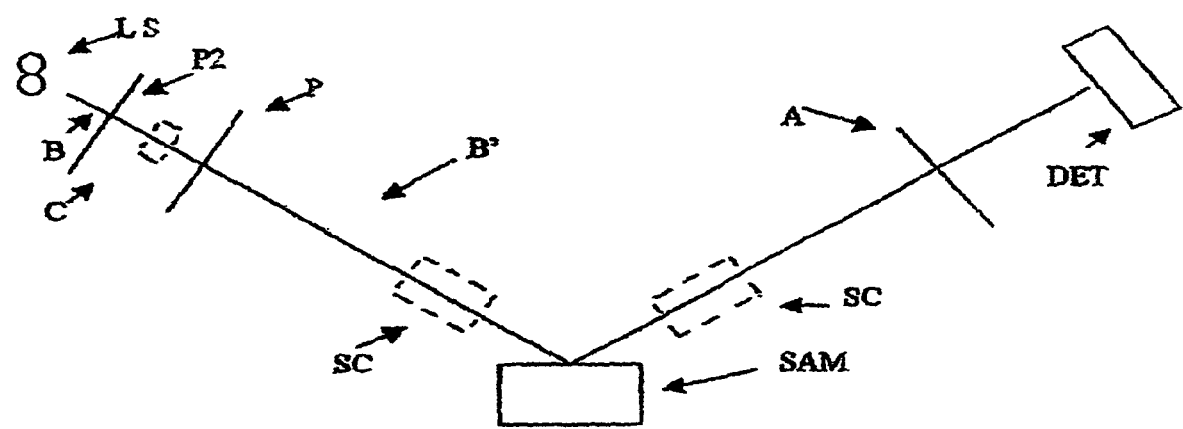
FIG. 1 shows a system for controlling the intensity of a beam of electromagnetic radiation comprising a Source (LS) of a Beam (B) of Electromagnetism, a Control Polarizer (P2), an optional Control Compensator (C), a Beam Polarizer (P), a Sample (SAM), an Analyzer (A) and a Detector (DET).
Figure 2:
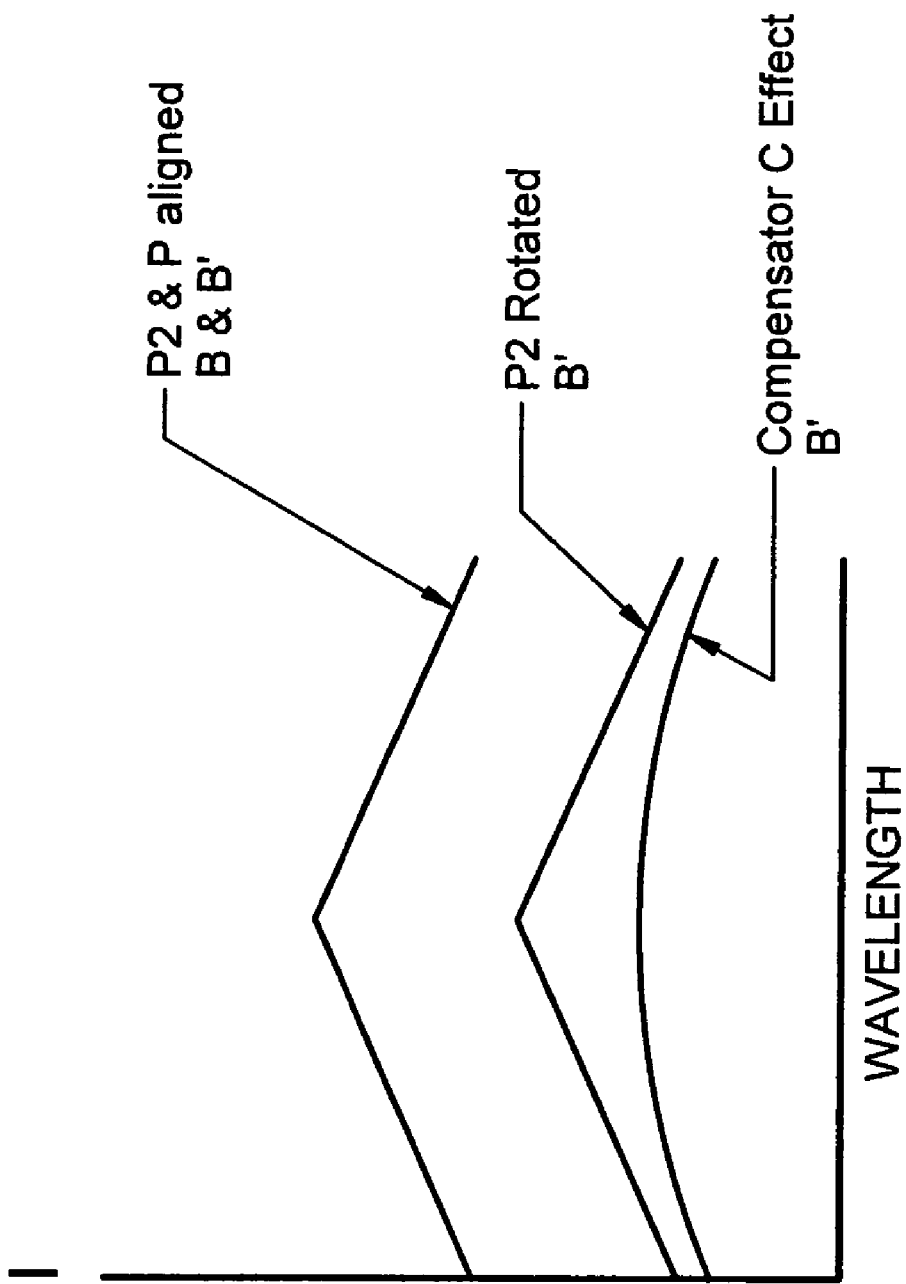
FIG. 2 shows an arbitrary demonstrative effect on Intensity (I) of a Beam (B') as compared to the Intensity of Beam (B) provided by a Source (LS) in FIG. 1.

FIG. 1 shows a Source (LS) of a Beam (B) of Electromagnetism, a Control Polarizer (P2), an optional Control Compensator (C), a Beam Polarizer (P), a Sample (SAM), an Analyzer (A) and a Detector (DET). FIG. 2 shows an arbitrary demonstrative effect on Intensity (I) of a Beam (B') as compared to the Intensity of Beam (B) provided by a Source (LS). Note the baseline Intensity (I) when said Control and Beam Polarizers (P2) and (P) aligned, and that rotating the Control Polarizer (P2) with respect to the beam Polarizer (P) has a uniform effect over the Wavelength Spectrum. Adding a Control Compensator (C) can cause selective increased attenuation of the mid-wavelength region and provide a more uniform Intensity Spectrum. Note also that at least one System Compensator (SC) can be incorporated into the system.

It is also disclosed that rotation of the Control Polarizer (P2) or Control Compensator (C) can be automated, optionally via a feedback circuit.

Figure 3:
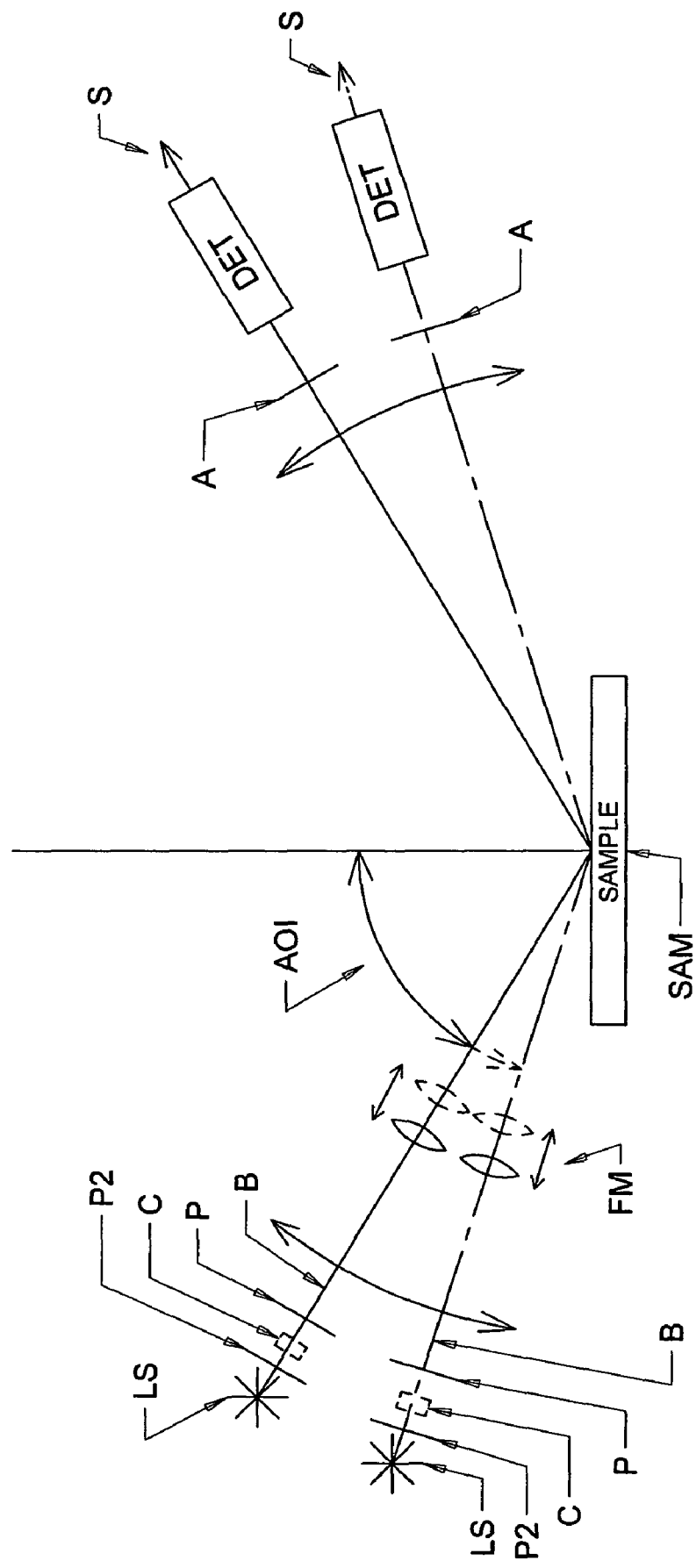
FIG. 3 shows a system for practicing the present invention methodology of investigating materials demonstrating low specular reflectance, using electromagnetic beams.

FIG. 3 shows a system comprising:
- a Source (LS) of electromagnetic radiation;
- a Control Polarizer (P2);
- a Control Compensator (C);
- a polarizer (P);
- a variable Focusing Means (FM);
- a Sample (SAM);
- an Analyzer (A);
- a Detector (det) of electromagnetic radiation;

arranged such that said Source (LS) of electromagnetic radiation provides a Beam (B) of electromagnetic radiation which is directed to pass through said Control Polarizer (P2) and Control Compensator (C), said Polarizer (P) and variable focusing means (FM) and impinge on said Sample (SAM) at an angle of incidence (AOI) thereto, partially reflect from said Sample (SAM), pass through said Analyzer (A) and enter said Detector (DET) of electromagnetic radiation such that said detector develops an output signal (S). Note that the angle of incidence (AOI) and Focusing Means (FM) are shown as being variable. Said system can be used to investigate low specular reflectance and/or depolarizing samples under the methodology of the present invention.

In the foregoing it is to be understood that at a high angle of incidence the focusing means can be used to reduce the aspect ratio of a beam spot on the sample, or the focusing means can be used increase a beam spot size to incorporate more area of a sample therein. The later would probably be done when a lower angle of incidence is used.

Also, it is noted that depolarization can result from back-side reflections, a non-uniform thickness sample film as well as be simulated by light from outside a beam. Where this becomes an important effect, the angle of incidence (AOI) and/or Focusing Means (FM) can be adjusted to control the effect, perhaps in conjunction with adjustment of a provided variable filter can be a neutral density filter and/or Control Polarizer (P2) and Control Compensator (C)

It is noted while application of the Control Polarizer (P2) and Control Compensator (C) can be applied to attenuate beam intensity which is incident on a Sample (SAM), and control of the angle of incidence (AOI) and/or Focus Means (FM) applied to increase intensity entering the detector (DET), it is possible that in some cases control of the angle of incidence (AOI) and/or Focus Means (FM) might also decrease intensity entering the detector (DET). It is the combined effect of said adjustments on intensity entering the Detector (DET) which is important in the present invention.

Itis also mentioned, generally, that an ellipsometer used to acquire data can be aligned using a specularly reflecting sample prior to investigating a non-speculalry reflecting sample therewith; that a sample can be rotated about an axis perpendicular to the surface thereof during data collection; that an investigated sample can be positioned along a normal to the surface thereof; that large a spot size to effect a "flood light" effect can be of benefit when investigating a non-speculatly reflecting sample, but that it is of benefit to avoid reflections from a sample supporting stage. It has also been noticed in some procedures that angles-of-incidence above about 80 degrees are associated with better signal-to-noise ratios, and it is noted that where the crossed-polarizer system is applied to control intensity, it can be automatically adjustment via a feed-back loop, which can be on a wavelength by wavelength basis.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of investigating materials demonstrating depolarization using electromagnetic beams, comprising a procedure which comprises steps a, b and c, said steps a, b and c being:

a) providing a system comprising:
   - a source of electromagnetic radiation;
   - a polarizer;
   - a variable focusing means;
   - a depolarizing material sample;
   - an analyzer;
   - a detector of electromagnetic radiation;

arranged such that said source of electromagnetic radiation provides a beam of electromagnetic radiation which is directed to pass through said polarizer, said variable focusing means and impinge on said depolarizing sample at an angle of incidence thereto, partially reflect from said depolarizing material sample, pass through said analyzer and enter said detector of electromagnetic radiation such that said detector develops an output signal;

b) while monitoring said output signal from said detector and determining depolarization of the beam entering thereinto therefrom from:

$$\% \, DEP = 1 - \sqrt{N^2 + C^2 + S^2}$$

where:
   $N = \cos(2\psi)$;
   $C = \sin(2\psi)\cos(\Delta)$; and
   $S = \sin(2\psi)\sin(\Delta)$;

varying the angle of incidence and degree of focusing provided by said variable focusing means, to determine a combination thereof which substantially minimizes depolarization associated with an output signal;

c) with the system configured as determined in steps a and b, obtaining data from the detector;

said method further comprising steps d and e, said steps d and e being:

d) practicing steps a and b to the end that the detector signal output represents an acceptable range of beam depolarization less than 35%, and e) obtaining data from said detector by practice of step c;

said method being characterized by at least one selection from the group consisting of:
   at least some obtained data is stored in machine readable media;
   at least some obtained data is displayed electronically or by non-electronic means;
   at least some obtained data is caused to be represented by a signal which is applied to provide a concrete and tangible result.

2. A method as in claim 1, wherein the angle of incidence is caused to be greater than about 75 degrees.

3. A method as in claim 1 in which said procedure further comprises providing at least one selection from the group:
   a variable filter between said source of electromagnetic radiation and said detector;
   a system comprising a control polarizer and a beam polarizer between said source and said sample; and
   a system comprising a control polarizer, a control compensator and a beam polarizer between said source and said sample;

which can be applied to control the intensity of the electromagnetic radiation entering said detector;

and in which said method further includes the step of:
   adjusting the selection to place the intensity of said electromagnetic radiation entering said detector into a range which does not saturate it.

* * * * *